US007689366B2

(12) United States Patent
Duck et al.

(10) Patent No.: US 7,689,366 B2
(45) Date of Patent: Mar. 30, 2010

(54) INTEGRATED SYSTEM FOR HIGH THROUGHPUT CAPTURE OF GENETIC DIVERSITY

(75) Inventors: Nicholas B. Duck, Apex, NC (US);
Michael G. Koziel, Raleigh, NC (US);
Nadine Carozzi, Raleigh, NC (US);
Brian Carr, Raleigh, NC (US); Tracy Hargiss, Cary, NC (US)

(73) Assignee: Athenix Corporation, Research Triangle Park, NC (US)

( * ) Notice: Subject to any disclaimer, the term of this patent is extended or adjusted under 35 U.S.C. 154(b) by 1243 days.

(21) Appl. No.: 10/386,401

(22) Filed: Mar. 11, 2003

(65) Prior Publication Data

US 2004/0014091 A1 Jan. 22, 2004

Related U.S. Application Data

(60) Provisional application No. 60/363,388, filed on Mar. 11, 2002.

(51) Int. Cl.
*G06F 19/00* (2006.01)
*C40B 30/00* (2006.01)
*C40B 30/02* (2006.01)

(52) U.S. Cl. .............................. 702/20; 702/19; 506/7; 506/8

(58) Field of Classification Search ...................... None
See application file for complete search history.

(56) References Cited

U.S. PATENT DOCUMENTS 6,022,716 A * 2/2000 Chumakov et al. ........ 435/91.42
6,455,254 B1 * 9/2002 Short .............................. 435/6
6,640,192 B2 * 10/2003 Collins et al. ................. 702/20

FOREIGN PATENT DOCUMENTS

WO WO 98/26407 A2 6/1998
WO WO 01/14417 * 3/2001

OTHER PUBLICATIONS

Definition from The Dictionary of Cell and Molecular Biology, Third Edition, Eds. J.M. Lackie and J.A.T. Dow, 1999, Academic Press.*
Altier, C., and Suyemoto, M., "A Recombinase-based Selection of Differentially Expressed Bacterial Genes," *Gene*, 1999, pp. 99-106, vol. 240, Elsevier.
Claverie, J., "A Streamlined Random Sequencing Strategy for Finding Coding Exons," *Genomics*, 1994, pp. 575-581, vol. 23.
Frengen, E., et al., "A Modular, Positive Selection Bacterial Artificial Chromosome Vector with Multiple Cloning Sites," *Genomics*, 1999, pp. 250-253, vol. 58.

Gay, P., et al., "Positive Selection Procedure for Entrapment of Insertion Sequence Elements in Gram-Negative Bacteria," *Journal of Bacteriology*, Nov. 1985, pp. 918-921, vol. 164(2).
Henikoff, S., et al., "Finding Protein Similarities with Nucleotide Sequence Databases," *Methods in Enzymology*, 1990, pp. 111-132, vol. 183.
Kamb, A., et al., "Software Trapping: A Strategy for Finding Genes in Large Genomic Regions," *Computers and Biomedical Research*, 1995, pp. 140-153, vol. 28.
Longmire, Jonathan, et al., "11.pUC-SV: A New Double Adaptor Plasmid System for Sequencing Complex Genomes," *Research Abstracts 2000 DOE Human Genome Program*, Bioscience Division and DOE Joint Genome Institute, Los Alamos National Laboratory, Los Alamos, NM.
Peterson, D., et al., "Efficient Capture of Unique Sequences from Eukaryotic Genomes," *Trends in Genetics*, 2002, pp. 547-550, vol. 18(11).
Altschul, S.F., et al., "Basic Local Alignment Search Tool," *J. Mol. Biol.*, 1990, pp. 403-410, vol. 215.
Altschul, S.F., et al., "Gapped Blast and PSI-Blast: A New Generation of Protein Database Search Programs," *Nucleic Acids Research*, 1997, vol. 25(17), pp. 3389-3402.
Dennis, C., "Error Reports Threaten to Unravel Databases of Mitochondrial DNA," *Nature*, Feb. 20, 2003, vol. 421, pp. 773-774.
Fickett, J.W., et al., "Development of A Database for Nucleotide Sequences," *Mathematical Methods for DNA Sequences*, 1989, Chapter 1, pp. 1-34, Waterman, M.S. (Ed.), CRC Press, Inc., Boca Raton, Florida.
Nicholas, H.B., et al., "Strategies for Searching Sequence Databases," *BioTechniques*, 2000, vol. 28(6), pp. 1174-1191.
Nedelcu et al. (2000) "The Complete Mitochondrial DNA Sequence of *Scenedesmus obliquus* Reflects an Intermediate Stage in the Evolution of the Green Algal Mitochondrial Genome" *Genome Research* 10:819-831.

* cited by examiner

*Primary Examiner*—Lori A Clow
(74) *Attorney, Agent, or Firm*—Alston & Bird LLP

(57) ABSTRACT

Compositions and methods for rapid and highly efficient characterization of genetic diversity in organisms are provided. The methods involve rapid sequencing and characterization of extrachromosomal DNA, particularly plasmids, to identify useful nucleotide sequences. The method involves generating a library of extrachromosomal DNA clones, sequencing a portion of the clones, comparing the sequences against a database of existing DNA sequences, using an algorithm to select novel nucleotide sequences based on the presence or absence of the sequence in a database, and identification of at least one novel nucleotide sequence. The DNA sequence can also be translated in all six frames and the resulting amino acid sequences compared against a database of protein sequences. Organisms of particular interest include, but are not limited to bacteria, fungi, algae, and the like. Compositions comprise a mini-cosmid vector comprising a stuffer fragment and at least one cos site.

22 Claims, 4 Drawing Sheets

INTEGRATED SYSTEM FOR HIGH THROUGHPUT CAPTURE OF GENETIC DIVERSITY

CROSS REFERENCE TO RELATED APPLICATION

This application claims the benefit of U.S. Provisional Application Ser. No. 60/363,388, filed Mar. 11, 2002, the contents of which are herein incorporated by reference in their entirety.

FIELD OF THE INVENTION

Methods to capture biological diversity in the form of genes encoding novel enzymes and proteins of commercial value are provided. Additionally, novel methods to rapidly sample and screen bacterial genomes for novel genes of interest are described.

BACKGROUND OF THE INVENTION

Increasingly, bacterial genes are being used in various industrial and agricultural applications such as insect resistant crops, herbicide tolerant crops, or improved industrial processes. Bacteria are capable of carrying out virtually every known biochemical process and are therefore a good source of proteins and enzymes for use in a wide variety of commercial processes. Bacterial genes of utility include those that encode proteins with insecticidal activity, those that catalyze industrial processes, proteins responsible for antibiotic resistance and virulence factors. While use of biologically derived genes and proteins is increasing, it remains a cumbersome process to discover and characterize genes encoding proteins which are viable for commercial application. Traditional approaches to identify commercially viable genes and proteins have relied on following the function of interest. Newer genomics approaches have attempted to sequences genes as quickly as possible and identify their function by homology to known genes. It remains unclear how efficient it is to sequence entire genomes of a given organism to identify new genetic activities. Efforts to characterize the genomes of organisms have been ongoing since tools of molecular biology became available for this purpose. These studies often look at the relatedness of different species or at the degree of difference between two or more organisms. There have been no systematic efforts to characterize the specific genes carried by plasmids, small discrete genetic elements of bacteria, and to use such characterization as a means to rapidly identify bacterial genes with commercial applications.

Bacterial species often carry genetic elements called plasmids that include a variety of genes. Often these plasmid encoded genes give the strain of a given bacterium commercially important characteristics. For instance, many *Bacillus thuringiensis* (Bt) strains are used as microbial pesticides. The genes responsible for producing the insecticidal proteins of these strains are plasmid encoded. Bt strain HD-1 has been used for decades as a microbial spray against various *lepidopteran* pests. Since many genes of commercial utility reside on the plasmids, not within the chromosomal DNA, whole-genome based genomics approaches to discover new genes are inefficient because one repeatedly sequences the chromosomal DNA. A number of techniques have been developed to increase the efficiency of gene discovery.

The use of microarrays allows comparison of several species (the test strains) to a known, sequenced species (the reference strain). In order to perform this method, one must generate the entire DNA sequence of a genome (the reference genome), then synthesize oligonucleotides corresponding to much of the reference genome, and imbed these oligonucleotides onto a matrix, such as a chip. One drawback of this method is that one must have the DNA sequence of a closely related reference strain. Only regions of similarity are identified while regions of non-similarity must be inferred. Furthermore, this method does not provide a method to determine nucleotide sequences of the variant regions present in the test strain.

Polymorphism mapping involves digestion of the genome with rare restriction enzymes and separation of the resulting fragments on pulsed field (PFGE) or field inversion gels (FIGE). This method can be used to screen related strains to determine the relative level of relatedness, and to map regions that are dissimilar between strains. However, this method does not generate any sequence information about the novel regions present in strains.

Differential hybridization techniques have the ability to identify regions of difference between strains, and to identify clones likely to contain differences. However, differential hybridization techniques are well known for their technical difficulty. The presence of repetitive DNA elements in genomes can substantially interfere with this method. While differential hybridization techniques based on hybridization of bulk PCR reactions are somewhat more technically feasible, none of these techniques has been used for rapid testing and characterization of plasmid sequences.

Because of the enormous genetic diversity among bacterial plasmids, methods are needed to facilitate the rapid and efficient identification of useful nucleotide sequences. There is a need to identify more bacterial genes with commercial relevance for such applications and to do so rapidly and efficiently.

SUMMARY OF INVENTION

Methods for rapid and highly efficient characterization of genetic diversity in organisms are provided. The methods involve rapid sequencing and characterization of extrachromosomal DNA, particularly plasmids, to identify and isolate useful nucleotide sequences. The method targets plasmid DNA and avoids repeated cloning and sequencing of the host chromosome, thus allowing one to focus on the genetic elements carrying maximum genetic diversity. The method involves generating a library of extrachromosomal DNA clones, sequencing a portion of the clones, comparing the sequences against a database of existing DNA sequences, using an algorithm to select said novel nucleotide sequence based on the presence or absence of said portion in a database, and identification of at least one novel nucleotide sequence. The DNA sequence can also be translated in all six frames and the resulting amino acid sequences can be compared against a database of protein sequences. The integrated approach provides a rapid and efficient method to identify and isolate useful genes. Organisms of particular interest include, but are not limited to bacteria, fungi, algae, and the like.

The sampling methods above can be used to rapidly identify and clone novel genes that have homology to existing genes. Novel genes are identified by this method. These novel genes would be difficult if not impossible to identify by other methods, such as hybridization. Included in this invention are methods to identify novel delta-endotoxin genes, novel cellulase genes, and the like. The sampling methods above can also be used to identify novel genes that have little homology to existing genes.

Compositions comprise a mini-cosmid vector comprising a stuffer fragment and at least one cos site. This vector is useful for generating a library of DNA clones with reduced insert sizes relative to conventional cosmid or fosmid vectors. This reduced insert size is useful for generating libraries of extrachromosomal DNA which may range in size from 0-200 kb or more.

DETAILED DESCRIPTION

The invention describes a method to rapidly characterize the genetic diversity in microorganisms and identify genes and nucleotide sequences of commercial interest, without the need for sequencing the entire genome. This method involves a unique coupling of several techniques to create an integrated strategy; generation of libraries with inserts of specific sizes, sampling of sequences, use of algorithms to pick clones most likely to have novel sequences, followed by methods for efficient sequencing of novel clones. The method provides for the rapid sampling of genetic diversity and permits identification of genes and nucleic acid molecules that may not be identified by hybridization or other available methods. Use of the method provides for rapid discovery of new genes and proteins.

Rapid methods for identifying novel nucleotide sequences from extrachromosomal DNA in a host organism are provided. While the methods are described generally in terms of characterizing bacterial extrachromosomal DNA, the method is applicable to any host organism as well as to direct isolation of DNA from environmental sources such as soil, water, and the like. Direct isolation removes the necessity of culturing the organism or strain prior to isolation of DNA. Host organisms from which the libraries may be prepared include prokaryotic microorganisms, such as Eubacteria and Archaebacteria, lower eukaryotic microorganisms such as fungi, some algae and protozoa, as well as mixed populations of plants, plant spores and pollen.

The method involves an integrated strategy for isolation and identification of novel nucleotide sequences. By "novel nucleotide sequences" is intended nucleotide sequences that share less than about 30% homology, preferably less than about 60% homology, more preferably less than about 80% homology, most preferably less than about 90%, 91%, 92%, 93%, 94%, 95%, 96%, 97%, 98%, or 99% homology to any sequence in the database used for comparison.

Figure 1:
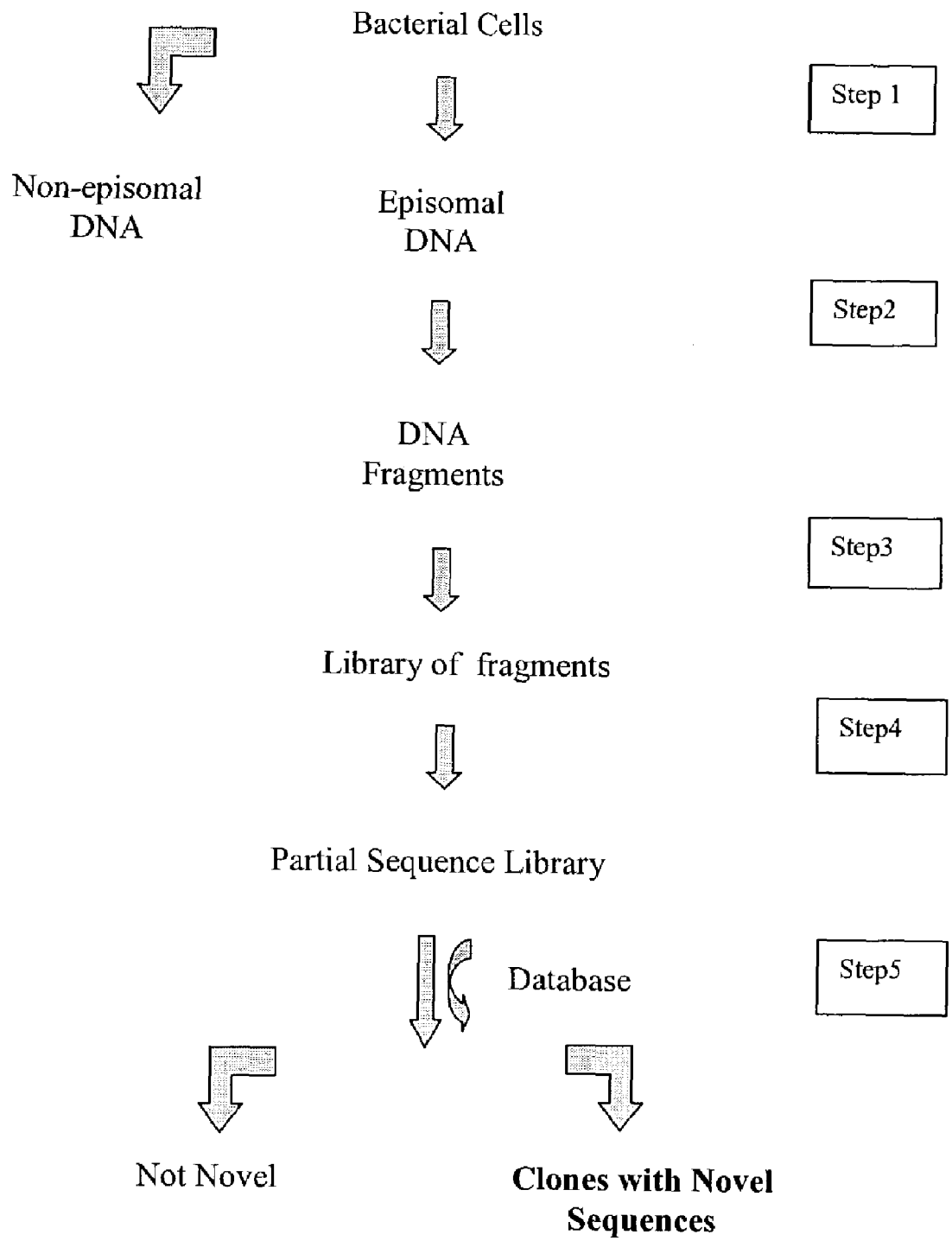
FIG. 1 provides a diagram of Phase I of an improved sequence capture strategy.

This method can be described as having two phases, Phase I and Phase II. In Phase I of the method, databases of plasmid sequences are generated by sequencing random clones of plasmid DNA. A schematic of the steps involved in Phase I is shown in FIG. 1. In Phase II, clones identified in Phase I are heavily sampled by sequencing to capture the sequence diversity present in these clones.

In one embodiment, the following steps are used to generate a database.

In Step 1, the DNA is prepared and enriched for extrachromosomal DNA. By "extrachromosomal DNA" is intended plasmids, extrachromosomal phage, linear plasmids, and any other extrachromosomal elements. In this step, DNA (from isolated bacteria, mixtures of bacteria, primary cultures of bacteria and other organisms such as fungi, or even DNA from environmental samples) is prepared by one of several methods known in the art to enrich for plasmid DNA (see Sambrook and Russell, Eds. (2001) *Molecular Cloning: A Laboratory Manual* (Laboratory Press, New York)). In one embodiment, DNA from individual organisms is released by cell lysis and plasmid DNA partially purified, by methods including gel electrophoresis, pulsed field electrophoresis (PFGE/field inversion gel electrophoresis (FIGE) (see, for example, Wang and Lai (1995) *Electrophoresis* 16:1-7), cesium chloride gradient centrifugation, alkaline lysis, purification of plasmid DNA by adhesion to and elution from a DNA binding column, or other methods know in the art to isolate DNA, specifically to isolate plasmid DNA from chromosomal DNA. The DNA can also be treated with DNA exonucleases that preferentially degrade open circular or linear DNA, but do not degrade closed circular DNA. DNA of a particular plasmid may also be purified by methods known in the art, such as, gel electrophoresis followed by excision of agarose fragments, and purification of DNA from the gel slice by methods known in the art (see Sambrook and Russell, supra).

In Step 2, the resulting DNA (referred to here as plasmid DNA) is then fragmented. It is important to note that the size of the fragmentation is such that large plasmids are cleaved, and represented as a heterogeneous population of different size molecules when analyzed by agarose gel electrophoresis. Small plasmids (less than the average size of the fractionated DNA purified) may or may not be incorporated in the resulting population of different size DNA molecules. Methods to fragment this DNA include sonication, partial digestion with DNAse, shearing by viscosity (e.g. passage through a nebulizer), and partial digestion with a restriction endonuclease (e.g. Sau3AI). It is important to determine a fractionation protocol that yields the correct size DNA fragments.

In one aspect, the ideal fragment size should be between about 10 to about 20 kb, and more preferably about 15 kb. This size is smaller than sizes typically used for genomic libraries. Using smaller DNA (e.g. 15-20 kb vs. 35-40 kb for typical cosmid libraries) has several advantages. First, shearing of DNA to smaller sizes will result in better representation of plasmid sequences then generation of libraries using larger fragments. This is because, unlike genomic DNA, plasmids are heterogeneous is size, and as a whole substantially smaller than circular bacterial genomes. It is important to allow plasmids of about 50 to 100 kb or larger to be represented efficiently in the resulting libraries. Second, generation of smaller fragments allows one to utilize DNA of lower quality than is required to generate large insert libraries. It is well known in the art that generation of large DNA inserts (e.g. for cosmid libraries) requires careful preparation of DNA to avoid randomly shearing DNA to size smaller than optimum for generating such libraries (150 kb or more; see Sambrook, supra). This can prove to be quite technically difficult, especially in preparing DNA from bacterial or eukaryotic cells that are hard to lyse, or for cells that produce large amounts of endonucleases. Thus, the smaller size inserts required for the methods of the invention relative to methods requiring very large molecular weight DNA facilitates library generation. Furthermore, coupling of DNA preparation with cloning in specialized vectors (e.g. mini-cosmid vectors as described below) allows for generation of libraries without the need to gel-purify DNA, further improving the throughput of library generation.

In another aspect of this invention, the DNA resulting from Step I is fractionated to yield smaller insert sizes of about 1 to about 5 kb. Purification of fragments of this size may be preferable in some instances. For example, this might be the preferred method when one expects the majority of episomal sequence obtained to be novel; or when one wishes to capture the entirety of the episomal sequences, and not exclude relatively small plasmids. In this aspect of the invention, the fragment size should be between about 1 to about 5 kb, and more preferably about 1.5 kb.

In some instances it may be advisable to generate DNA fragments smaller then 10-20 kb. (e.g. 5 kb). One can achieve this by using the methods illustrated in Step 2, by modifying the fragmentation conditions to yield smaller fragments. Since the DNA fragments isolated are smaller, this method will require a larger sequencing effort than a method generating a 15 kb insert; since a higher percentage of the clone is sequenced in step 4, and more clones must be analyzed to assure coverage of the diversity in any one strain. In this modified method, it may be preferable to clone the DNA fragments directly into a plasmid vector such as pBLUE-SCRIPT®(Stratagene) or a cDNA cloning vector such as LAMBDA ZAP®(Stratagene).

After fractionation, the resulting DNA molecules are separated (typically by electrophoresis through agarose gels) and the appropriate size fragments purified Methods to purify fragments are well known in the art. Examples of purification methods include treatment of gel slices with agarase (β-agarase), or chemical digestion of agarose followed by chromatography.

In Step 3, the fragments prepared in step 2 are ligated to a vector, and the resulting molecules transformed into bacteria such as *E. coli*. DNA ligation reactions are performed by methods known in the art (e.g., Sambrook and Russell, supra), usually by incubating a quantity of fragmented bacterial plasmid genome with a quantity of *E. coli* cloning vector (e.g. pBluescript from Stratagene) in the presence of T4 DNA ligase at 16° C. for 18 hours; or according to manufacturer's directions. Alternatively DNA may be ligated for at least 2 hours at about 25° C. Ligated DNA is transformed into a bacterial host by either electroporation or chemical transformation methods known in the art (see, for example, Sambrook and Russell, supra) Resulting colonies are picked, grown in liquid culture, and plasmid DNA prepared by methods known in the art.

In one aspect of this invention, the vector used is a common cloning vector, such as pBluescript (Stratagene). In other aspects of the invention, the cloning vector is specially designed to allow facile cloning of plasmid sequences (see "Mini-Cosmid Vectors", below). Ideally the vector will allow library fragments greater than about 5 kb, preferably up to about 25 kb. The vector used in the invention may be plasmid, phage, cosmid, phagemid, virus or selected portions thereof.

In Step 4, DNA is prepared from individual clones from the library, and a portion of the clone is sequenced. By "portion" is intended less than about 30% of the size of the clone. In general, this is accomplished by sequencing the ends of the insert DNA with primers that anneal to the DNA region adjacent (but outside the cloning region of the vector), and prime DNA synthesis into the insert DNA. A sample set of sequences is obtained from each clone. In general this is performed by preparing DNA from each clone, and then performing DNA sequencing reactions using primers that are adjacent to (and prime DNA synthesis in the direction of) the insert DNA fragment. For example, one can prepare 96 well plates containing media and inoculate each well with a colony representing a DNA clone. Multiple 96 well plates can be prepared in this manner. The resulting inoculated wells are grown (usually with shaking at 37° C. overnight) to saturation, and plasmid DNA prepared by methods known in the art (see, for example, Carninci et al. (1997) *Nucleic Acids Res*. 25(6):1315-1316) or by use of an automated 96-well miniprep kit protocol (QIAprep Turbo, QIAGEN).

In Step 5, the DNA sequence data resulting from step 4 is compared against a database of existing DNA sequences, including sequences of previous fragmented clones. By "existing DNA sequences" is intended DNA sequences that can be found in a public database, such as GENBANK®, PFAM, or ProDom. By "database" is intended a collection of data arranged for ease and speed of search and retrieval. The database can comprise either nucleic acid sequences and/or deduced amino acid sequences. The databases can be specific for a particular organism or a collection of organisms. For example, there are databases for the *C. elegans, Arabadopsis* sp., *M genitalium, M jannaschii, E. coli, H influenzae, S. cerevisiae* and others. In preferred embodiments, the database comprises only known endotoxin proteins. In another preferred embodiment, the database comprises only known lignocellulose-degrading enzymes. The database can be a public database, can comprise sequences obtained by end sequencing of various clones, or can be generated from genomic sequences. This comparison is performed with an algorithm designed to parse clones based on presence or absence of their partial sequences in the database. By "algorithm" is intended a recursive, computational procedure for solving a problem in a finite number of steps. By "parse" is intended to separate or sort into parts. Clones not having their partial sequences represented in the database are identified in this manner. These are referred to here as novel clones. The sequences are tested to identify novel sequences, likely to represent novel clones. This can be done by, for example, performing similarity searches against a database of all known sequences. Typically, this is performed by using the BLAST® series of algorithms (Altschul et al. (1990) *J. Mol. Biol.* 215:403-410; Altschul et al. (1997) *Nucleic Acids Res.* 25:3389-3402; Gish and States (1993) *Nature Genet.* 3:266-272). BLAST® algorithms compare a query sequence(s) for similarity to a database of known sequences and identifies sequences in the database(s) with highest scoring probability of similarity. The results of BLAST® searches are typically expressed by a 'BLAST® score' which is an expression of the probability of the two sequences NOT being truly similar. Thus, low BLAST® scores suggest high degrees of similarity. Proteins or DNA regions with identical amino acid or DNA similarity can yield scores of 0; suggesting the probability of the two sequences not being related is zero (since they are identical). High scoring BLAST® similarities often have values of $e^{-50}$ or greater. Selection of novel sequences can be done by empirical inspection of blast scores, and sorting of novel sequences (having no high scoring match in a blast search) from those sequences having blast scores likely to indicate identity (for example $P_0$ of $e^{-10}$ or $e^{-25}$ or $e^{-100}$ or greater). Alternatively, one can analyze batches of blast scores using algorithms designed to parse high scoring reads from low scoring reads. An example of the logic involved in such an algorithm is described in Example 3. The values of the BLAST® score cutoffs are intended to be exemplary. One can vary the cutoff values used without substantially reducing the value of the method. One way to determine the values to use for this procedure is by empirically setting values, running tests, and empirically determining the most useful values. Using such methods, one can quickly identify only the clones that have at least one and preferably two unique sequences (i.e. not previously identified in the database). Clones having one or more unique sequences are then sequenced in their entirety. In one embodiment, the nucleotide sequence is translated into all six reading frames to obtain all possible amino acid sequences and then the amino acid sequences are compared to a protein database.

One such program is BLAST®X. (Altschul et al. (1990) *J. Mol. Biol.* 215:403-410; Gish and States (1993) *Nature Genet.* 3:266-272) BLAST®X searches may be performed against a large set of known genes (for example, the GEN-BANK® database). Alternatively, such searches may be performed locally, against smaller databases containing genes of particular interest to the user.

While the algorithm may be a computer program, it is not critical to the invention that the algorithm be a computer program, or that if written as a computer program, that it be written in any particular computer language. For example, the algorithm may be as simple as a set of instructions for a person to utilize to identify and sort individual sequences by hand. Alternatively, such steps may be incorporated into a computer program. In one aspect of this invention, the algorithm is represented in a computer program written in C++, Java, or Basic programming language. It is understood that one may create such a program in one of many different programming languages. In one aspect of this invention, this program is written to operate on a computer utilizing a UNIX™ operating system. In this aspect, it is preferable if the computer program is designed to be compatible with DNA sequence assembly and analysis software. For example, Phred, Phrap, and Consed (Ewing et al. (1998) *Genome Research* 8:175-185; Ewing and Green (1998) *Genome Research* 8:186-194; Gordon et al (2001) *Genome Research* 11(4):614-625) are powerful programs used to sort DNA sequences by quality and assemble overlapping sequence reads. Consed (Gordon et al. (1998) *Genome Research.* 8: 195-202) is a program designed to allow editing and analysis of overlapping sequence reads generated by use of Phred and Phrap programs. It may be preferable to design the computer program to accept sequence files resulting from Phred/Phrap, Consed, or other DNA sequence assembly software.

In one aspect of this invention, one continues to sequence random clones, and does not institute phase II. In this aspect, one continues to sequence random clones to generate a database of diversity resulting from the extrachromosomal DNA of interest. This may be preferable when the number of unique sequences resulting from phase I is high, for e.g. greater than about 66% of resulting sequences.

Figure 2:
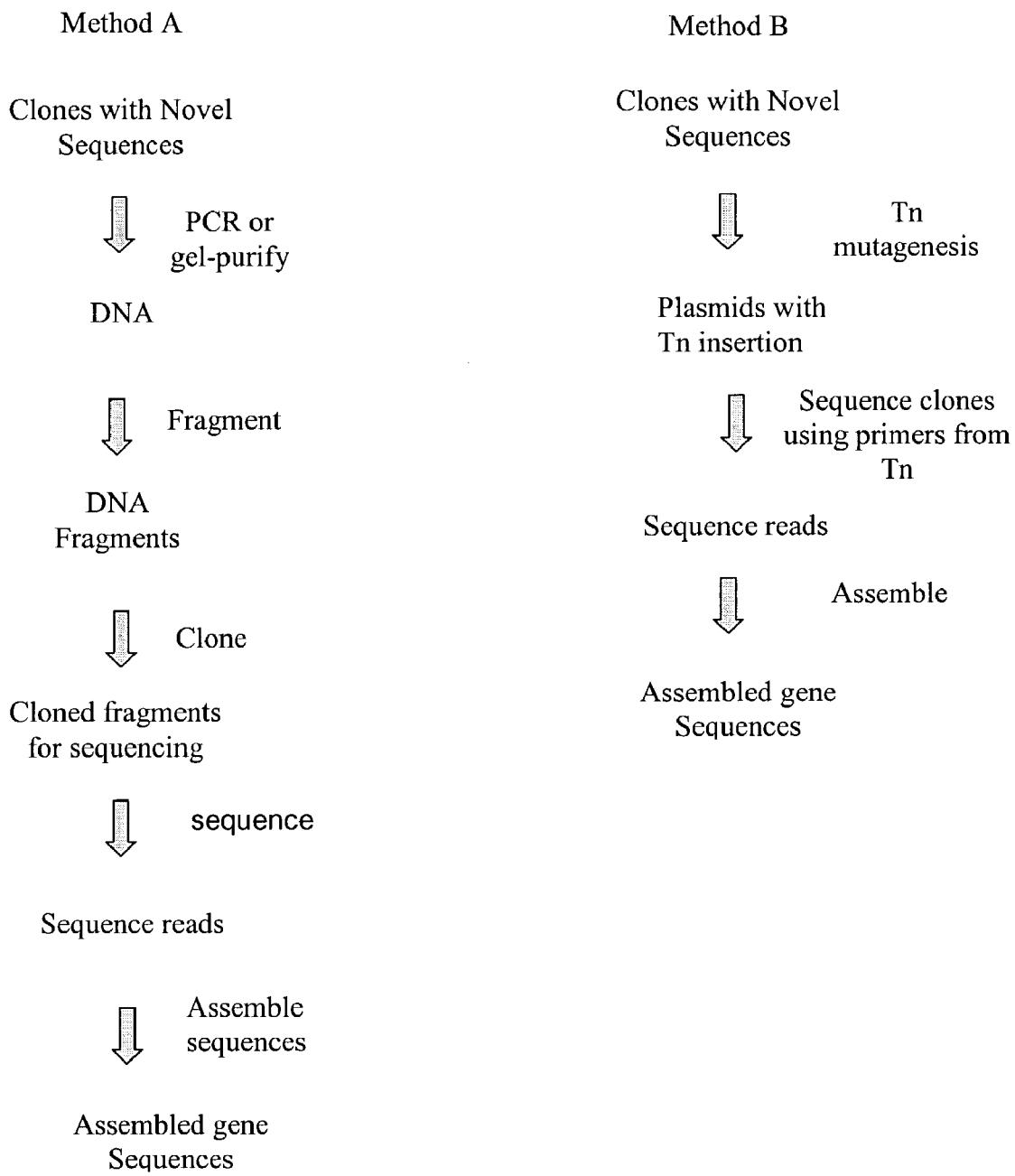
FIG. 2 provides a diagram of two methods for Phase II of an improved sequence capture strategy.
Figure 3:
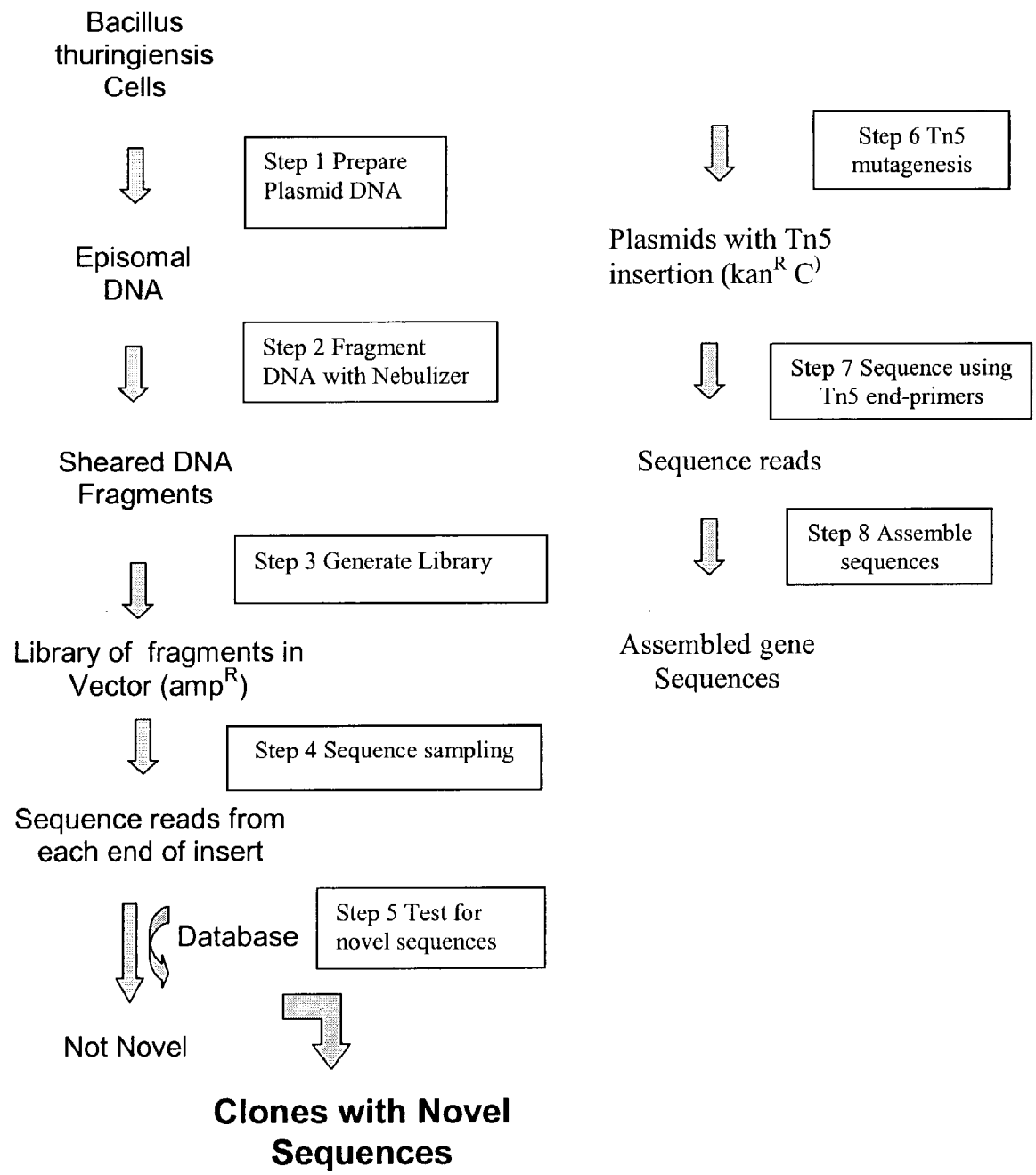
FIG. 3 provides an example of a sequence capture strategy to isolate novel clones.
Figure 4:
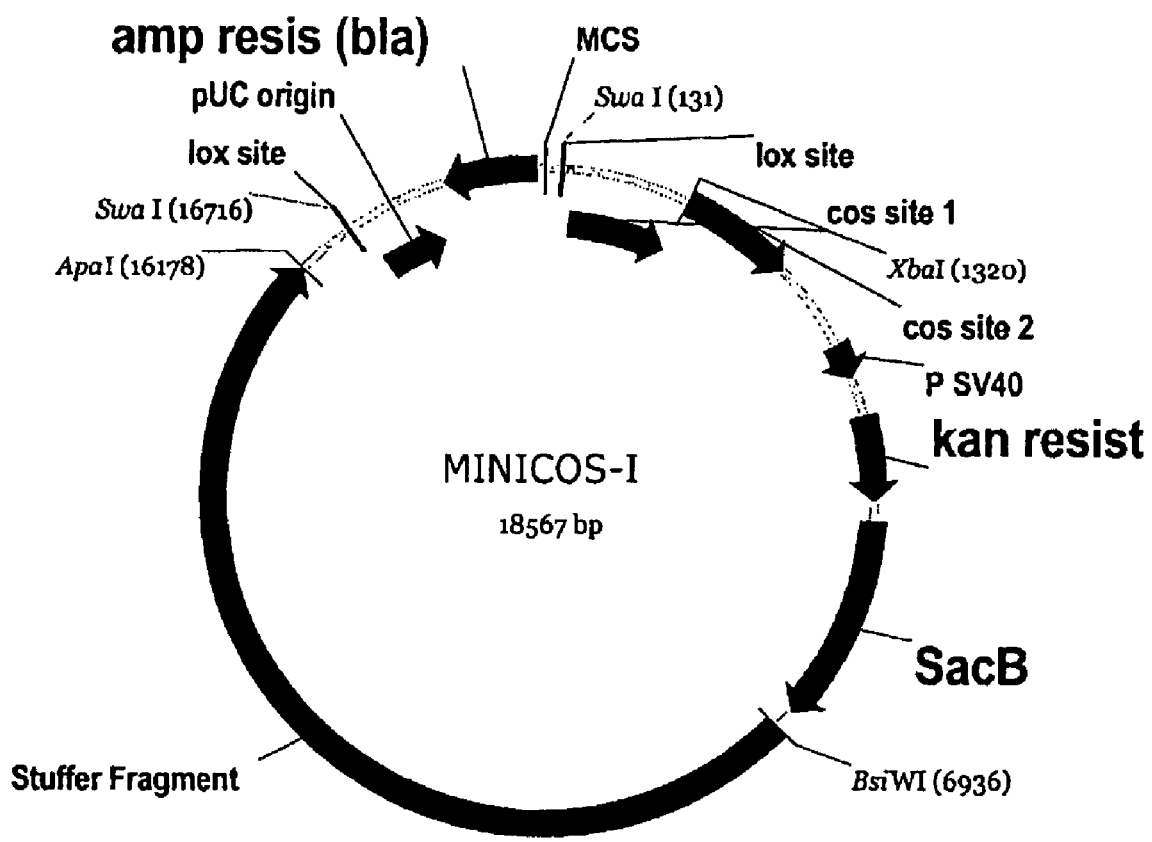
FIG. 4 shows a graphical map of minicos-I. Genes for ampicillin resistance (amp), kanamycin/neomycin resistance (kan) are shown, as well as location of multiple cloning sit (MCS), cos sites (cos), cre recombinase recognition sites (lox), and the origin of replication (pUC origin). Lox sites are organized such that incubation with cre recombinase yields to circular molecules, one of which contains the insert DNA, amp resistance, origin of replication, but lacks the stuffer fragment, kan resistance, and sacB gene.

In Phase II, the DNA sequences contained in the novel clones are obtained. This can be accomplished by one of several methods, which can result in generation of complete sequence of all genes contained in novel clones. Two methods by which this can be accomplished are illustrated in FIG. 2, 'Method A', and an alternative method, 'Method B'.

Method A involves generation of randomly sheared DNA fragments from novel clones to generate smaller DNA fragments (for example 1-3 kb), cloning of these DNA fragments to generate a library of sub-clones, and sequencing of a number of these sub-clones for each novel clone. A summary of the steps involved in Method A is shown in FIG. 2. For example, a particular 20 kb clone may be digested with restriction enzymes liberating the novel insert DNA. That DNA fragment is purified by gel electrophoresis, and fragmented to small fragments (1-3 kb preferably) by methods known in the art, and described in step 2 above. A number (e.g. 10-50) of the resulting subclones are then picked and their end sequences determined as in step 4 above. The resulting DNA sequences are assembled to generate the sequence of the 20 kb DNA fragment. It is important to note that for the purposes described in this disclosure, it is not necessary to generate complete, unambiguous DNA sequence for all nucleotides (or even a majority of the nucleotides) contained in this fragment.

Method B describes one aspect of the invention. In this aspect, a series of reactions are performed to generate the sequence from the novel clones in a rapid fashion. A summary of the steps involved in Method B are shown in FIG. 2.

In one aspect of Method B, the clones from step 5 are mutagenized with a transposable element in vitro (e.g. Tn5). The transposon system used inserts a transposable element that contains the DNA for an antibiotic resistance marker not otherwise present on the clones. Methods for mutating clones are well known in the art (see Sambrook, supra).

In most cases the order of the reactions can be inverted without hindering the outcome of the experiment. If the procedure involves transforming into *E. coli*, it is advisable to perform this step second.

Next, the sequences of each novel clone are obtained by preparing purified DNA from several of the Tn-insertion clones (10-50 per novel clone, depending on size of the original clone) and sequencing the insert DNA by priming DNA synthesis from the transposable element. Each random insertion of the transposon will generate a new primer binding site.

The resulting DNA sequences are compiled and the sequence of the novel clone determined.

Mini-cosmid Vectors

In one embodiment, the vector used for generating the library is a "mini-cosmid" vector. These vectors are defined predominately by the insertion of a large stuffer fragment between two COS sites; this allows one to generate "mini-cosmid" libraries. By "stuffer fragment" or "stuffer sequence" is intended a DNA fragment useful to control the size of the cloned insert within a vector. It is recognized that the size may vary to obtain clones of varying lengths. Generally, the stuffer fragment will have characteristics as described below.

These mini-cosmid libraries are prepared similarly to cosmid libraries, except that the presence of a large stuffer fragment alters the average insert size allowable from about 35 to about 40 kb to a smaller size, for example, about 15 to about 20 kb, or about 20 to about 25 kb of insert. The vectors designed and created for this purpose are referred to herein as mini-cosmid vectors. The size of the stuffer fragment will vary depending upon the preferred size of the insert. Generally, the stuffer fragment will range from about 5 to about 35 kb, including sizes of about 10 to about 30 kb, about 15 to about 25 kb, and about 20 kb.

These vectors use COS sites to allow size selection of inserts by packaging in phage, and therefore remove the need for gel purification of digested DNA. The stuffer fragment is located between the COS sites of the vector. This unique feature allows one to create libraries with reduced insert sizes relative to conventional cosmid or fosmid vectors. This reduced insert size is useful for generating libraries of bacterial plasmids, which may range in size from 0-200 kb or more (and usually 5-150 kb or more).

The stuffer fragment can be engineered to have several useful features. In one aspect of this method, the stuffer DNA contains the DNA encoding a functional copy of the *Bacillus subtilis* sacB gene (for example from the vector PRE112 (Edwards et al. (1998) *Gene* 207:149-157). sacB encodes a levansucrase that is toxic to gram-negative bacteria grown in the presence of sucrose; sacB activity leads to the formation of levan polymers that kill the cell. Thus, a stuffer fragment encoding sacB allows a way for one to select against presence of the plasmid, or more specifically the stuffer fragment, in *E. coli*.

Furthermore the stuffer fragment can be engineered to contain a copy of an antibiotic resistance gene, such as the chloramphenicol acyl transferase gene. Presence of such a gene can allow one to either select for clones containing this gene, or against constructs containing this gene by replica plating.

Furthermore the stuffer fragment can contain an origin of replication that confers ability of the resulting plasmid to replicate in hosts other than *E. coli*, including, for example, *Bacillus* and *Streptomyces* species.

Furthermore the boundaries separating the stuffer fragment from surrounding DNA can be designed to have features which allow one to remove the stuffer fragment from the plasmids at a time after packaging and transfection into *E.coli*. For example, one can engineer the boundaries of the stuffer fragment to have cleavage sites for one or several rare restriction enzymes, such as PmeI, PacI, SfiI, or an intron-encoded nuclease. Thus, digestion with this rare enzyme will excise the stuffer fragment without digesting the insert-containing vector anywhere else (i.e. in the insert DNA). The digested vector can then be relegated to create clones that now lack the stuffer fragment. This can be useful in preparing the DNA for subsequent analysis such as transposon mutagenesis.

Removal of the stuffer fragment may be useful where one wishes to perform methods that would be hindered by the presence of the stuffer, such as transposon mutagenesis. Furthermore the boundaries of the stuffer fragment can be designed to have sites recognized by site-specific recombinases, including transposases. One example of such a recombinase is the cre recombinase, which catalyzes recombination at specific nucleotide sites (lox sites). It is understood that many of the various known site-specific recombinases will function as a site specific recombinase system for the stuffer. Such recombinase systems include cre/lox system, Flip recombinase system (based on the recombinase for the yeast two micron plasmid), P1 phage based recombinases, (see for example, Stark et al. (1992) *Trends Genet.* 8:432-95). Hallet and Sherratt (1997) *FEMS Microbiol. Rev.* 21:157-78. Thus, one can remove the stuffer fragment by incubation of the vector in the presence of a site specific recombinase such as cre, either in vitro, or by passaging the vector through a strain expressing or inducible to express the cre recombinase.

The vectors of this invention provide a number of ways to remove the stuffer fragment from the vector after transfection into *E. coli*. The resulting plasmid is then transformed, transfected, electroporated, or otherwise transferred into *E. coli*, and clones having lost the stuffer fragment, but containing a transposon insertion (as judged by resistance to the antibiotic contained within the transposon) are identified. This results in the generation of a number of clones for each novel clone, with transposon insertions randomly distributed throughout the circular plasmid.

Techniques by which removal of the stuffer fragment can be accomplished include but are not limited to:

1. Digestion of DNA with a restriction enzyme, such that digestion with this enzyme cleaves at each end of the stuffer fragment.

2. Treatment of the DNA in vitro with a trans-acting site specific recombinase such as the cre recombinase. This method is useful in the case that the vector has lox sites flanking the stuffer DNA, and arranged in the proper orientation to excise the stuffer fragment 3. Transformation of the DNA into an *E. coli* strain that expresses the cre recombinase. (for example λKC: Elledge et al. (1991) *Proc. Natl. Acad. Sci. USA*, 88:1731-1735). This method is useful in the aspect in which the vector has lox sites flanking the stuffer DNA, and arranged in the proper orientation to excise the stuffer fragment. Clones identified in this strain as transformants are likely to have lost the stuffer fragment by cre-mediated deletion of the stuffer fragment.

4. Amplification of the novel DNA insert by PCR with a high fidelity thermostable polymerase (such as Pfu), and cloning the resulting PCR product into a vector that lacks the stuffer fragment, and has not been mutagenized with a transposon.

In principal, one can use fundamentally any DNA as a stuffer fragment. However, there are characteristics of the stuffer DNA that provide advantages over other possible choices. First, it is advantageous to use a stuffer fragment that has few restriction sites. Addition of such a large piece of DNA can create problems in identifying unique sites elsewhere in the insert containing clone. It is also important that the stuffer fragment not contain restriction sites for the critical restriction sites of the vector, such as the XbaI site that separates the COS sites, and the restriction enzymes in the polylinker.

Second, the stuffer fragment should be known to propagate in *E. coli*, and to lack origins of replication or large inverted repeats that would interfere with plasmid propagation, or cell growth.

Current vectors for cloning and analysis of DNA from prokaryotic organisms fall into the following classes.

General plasmid-based cloning vectors, such as pUC118 (Stratagene), pBS SK+ (Stratagene), are designed or cloning of small DNA inserts, usually one gene. These vectors are quite useful for cloning genes amplified by PCR, and many versions of such plasmids are commercially available by suppliers such as Stratagene, Promega, and Invitrogen. However, the ability of all insert sizes to replicate in these vectors, and the growth advantage of small inserts over larger insert sizes reduces their usefulness for use in the cloning of genomes. Cloning of genomic or other complex DNA into these vectors typically requires gel-purification or other size selection of the insert DNA to allow cloning of appropriate size inserts. Furthermore, when using these vectors, one tends to clone relatively small DNA fragments of about 0.5-10 kb, usually no more than 5 kb. The reduced size of genomic inserts increases the number of clones that must be screened to adequately cover the genome.

Cosmid vectors such as pWE15, allow cloning of fairly large DNA fragments (up to 40 kb) by the use of COS site to package ligated DNA into lambda. However, the DNA must be carefully prepared to obtain DNA of at least 100 kb, and preferably 150 kb. This is needed to ensure the fragmentation by partial digest yields two ends on each molecule that are digested with the restriction enzyme, and not sheared randomly. This DNA is typically gel-purified after digestion. Vectors such as Supercos (Stratagene), possess two COS sites, and therefore allow one to clone 15-40 kb inserts without gel purification; this is because inserts must be a minimum size to allow them to be packaged by lambda packaging extract. However, since the DNA cloned is so large, one must carefully prepare the DNA as for single COS vectors.

cDNA cloning vectors such as LAMBDA ZAP™ allow cloning of small inserts, up to 10 kb, by use of lambda packaging extracts. Phage can be manipulated, then induced to produce plasmid by induction of single-stranded DNA by superinfection with M13 helper phage, such as R408, followed by transfection into a fresh host strain (Short et al. (1988) *Nucleic Acids Research* 16:7583-7600).

Mini-cosmid vectors are useful in the rapid generation of libraries of medium to large insert size. The ability to package the insert DNA after phosphatase treatment, and without size selection provides a speed and insert size advantage over plasmid-based cloning, and allows library construction with lower quality DNA inserts than is required for cosmid library or BAC library construction. Mini-cosmid vectors allow excision of the insert as a minimal vector, containing an antibiotic resistance gene (e.g. ampicillin resistance) a colE1 origin of replication. To facilitate size reduction of the mini-cosmid clones, several features are designed into the vector.

In one embodiment, the minimal vector is flanked by recombination sites, for example lox or frt sites, organized such that incubation of a full insert containing mini-cosmid clone with, for example, the Cre recombinase results in excision of the minimal vector. Excised minimal vector can be selected by plating on antibiotic (such as ampicillin) and counter selecting by plating on sucrose. Thus, only clones that maintain amp and have lost SacB function will grow. One can further confirm the excision by plating amp resistant clones onto kanamycin. Since kanamycin resistance resides outside of the minimal vector, the clones should be ampicillin resistant, sucrose sensitive, and kanamycin sensitive.

As an alternative to use of recombination sites, mini-cosmid vectors contain a series of restriction enzyme sites at the border of the minimal vector. Thus, one can reconstitute the minimal vector by digesting with one or more of these enzymes, diluting the digestion mixture, re-ligating the diluted digestion mixture, and transforming this mixture into a cell. One may then select for formation of the minimal vector as described for recombination sites above.

Further Methods

In one aspect of the invention, one may further identify DNA regions surrounding the novel clone. For example, one may accomplish this by generating hybridization probes and screening an existing DNA library (such as the library sequenced in Phase I). Alternatively, one may generate a library of larger inserts (for example a cosmid library), and screen for clones likely to contain DNA adjacent to the novel clone of interest. Alternatively, one may use one of many methods to identify sequences adjacent to clones. For example, one may clone and sequence regions flanking a known DNA by inverse PCR (Sambrook and Russell, supra). Another such method involves ligating linkers of known sequence to genomic DNA digested with restriction enzymes. Then generating PCR product using a oligonucleotide homologous to the oligo linker, and an oligo homologous to the region of interest (e.g. the end sequence of a novel clone). A kit for performing this procedure (GENOMEWALKER®) is available from Clonetech.

The method described here is useful for generating large datasets containing gene sequences of commercial value. For example, it is well known that insecticidal proteins, such as the *Bacillus thuringiensis* delta-endotoxin genes, are found predominately on large extrachromosomal plasmids. Thus isolation and sequencing of plasmids from *Bacillus* strains, such as *Bacillus thuringiensis* strains is likely to lead to identification of novel delta-endotoxin genes. Such genes are likely to be valuable for controlling insect pests. Furthermore, many *Clostridia* strains are known to have large extrachromosomal plasmids, and some of these are known to contain virulence factors, as well as toxins such as iota toxin (see, for example, Perelle et al. (1993) *Infect. Immun.* 61(12):5147-5156, and the references cited therein). Furthermore, it has been shown that the majority of variability for *Clostridia* strains appears to occur due to plasmid content (see, for example, Katayam et al. (1996) *Mol. Gen. Genet.* 251:720-726). Thus, sequencing of the plasmids of multiple *Clostridia* strains will quickly capture a large amount of genetic diversity. There has been report of a homolog of delta-endotoxin gene present in *Clostridia* sp. (Barloy et al. *J. Bacteriol.* 178:3099-3105).

Tumor-inducing and symbiotic plasmids are common in *Agrobacterium* and *Rhizobium* strains (e.g., Van Larebeke et al. (1974) *Nature* 252:169-170). Thus sequencing of bacterial plasmids, especially those from known plant pathogens, is likely to identify genes involved in plant-pathogen interactions including genes involved in or required for both virulence and avirulence.

Much of the diversity present in bacterial populations is present on plasmids. Many of plasmids are known to contain virulence factors, important for infectivity or severity of infection by bacteria pathogens. Correspondingly, it is likely that many of the proteins expressed by plasmid genomes are likely to have value as vaccines. For example, both plasmids pXO1 and pXO2 of *Bacillus anthracis* encode proteins required for pathogenesis during anthrax infection. pXO2 encodes proteins that produce a protective capsule around the bacterium. The pXO1 plasmid encodes the three proteins of the anthrax toxin complex, lethal factor (LF), edema factor (EF), and the protective antigen (PA). The PA protein (protective antigen) forms the basis of a vaccine for anthrax. The quick and efficient sequencing of bacterial plasmids will yield information with which one can create a database of proteins that might serve as effective vaccines.

The methods are useful for strain identification and typing. Not only are bacterial plasmids a vital component of the diversity of bacterial subspecies, they contribute substantially to the genetic differences between closely related strains. Plasmids are known to be transferable between related strains, and can result in modified characteristics such as ability to produce toxins, etc. Thus there is commercial value in developing diagnostic tools based on plasmid sequences. DNA sequences generated by this method can be used for generating diagnostic tools. These diagnostic tools can be created by comparing DNA sequences of plasmids obtained by this method, identifying either unique sequence regions, or regions shared by groups of plasmids one wishes to identify. Oligonucleotides corresponding to the identified regions can then be synthesized by methods known in the art, and used to establish PCR-based strain typing methods.

In the same manner, the methods can be used in medical diagnostics, that is, for the detection and identification of typing of infectious agents.

The present method is useful for analyzing the contribution of extrachromosomal DNA for example, bacterial plasmids, to genome diversity. (Ng et al. *Genome Research* 8:1131-1141) sequenced the 191 kb 'dynamic replicon' from a halophilic archaeon and found the presence of 1,965 ORFs of 15 bp or larger.

A survey of *Closdridium perfringens* strains concluded that serological variation as well as changes in pathological spectrum may be entirely due to loss, or acquisition of extrachromosomal elements (Canard et al. (1992) *Mol. Microbiol.* 6:1421-1429). A separate article provides further evidence for substantial amount of bacterial strain variation as plasmid borne. (Katayam et al. (1996) *Mol. Gen. Genet.* 251:720-726).

Strain variation due to plasmid content is also well known for *Bacillus* strains, particularly *Bacillus thuringiensis*. For example, Carlton and Gonzales (1984) "Plasmid-Associated Endotoxin Production in *Bacillus thuringiensis*" in *Genetics and Biotechnology of Bacilli*, eds. Ganesan and Hoch (Academic Press).

Isolation and sequence of plasmid DNA specific to bacteria has several advantages over current methods for gene identification. First, since genes are identified by DNA sequence, this method is more likely to identify genes with lower DNA similarity to known genes than can readily be accomplished by hybridization. Second, since the plasmid genomes of strains will be a fraction of the total genome size (1-20%), it will be possible to rapidly sample the genomes of many related bacteria, and quickly identify interesting genes. Third, since much of strain to strain variation exists due to plasmid differences; this method will be very efficient at capturing the major diversity differences in bacterial groups. Furthermore the efficiency of the method increases as the size of the existing sequence data set increases (see Table 3). As the percent of novel clones detected drops from 50% to 1% the efficiency of the method increases from 3-fold to 16-fold relative to sequencing the bacterial genome (for a 15 kb insert size, see Table 3).

Though only specific bacterial species are described herein, it is understood that virtually all bacteria are likely to contain plasmid or episomal DNA, and that plasmid DNA can be selected from these bacteria and utilized in the method to identify novel genes. Furthermore, it is understood that one need not necessarily have purified the bacteria or other cell in order to isolate and analyze its plasmid content; i.e. this method can be applied to samples from mixed populations, or of unknown origin, such as environmental samples.

While many of the commercial uses of the resulting sequences can be apparent from direct inspection of the resulting sequences, one may perform additional steps to identify further commercial uses of the resulting sequences or genes.

First, the sequences are compared by DNA and amino acid homology to public and private gene databases, to identify any genes that are likely to be homologous to known commercial proteins. This method can also identify characteristics of otherwise novel proteins, for example, presence of common functional protein motifs such as ATP-binding domains, transmembrane regions, etc.

Second, the genes can be cloned into expression vectors in order to produce proteins. For example, one may amplify the genes by PCR and clone them into an expression vector such as pGEX (New England Biolabs), transform this construct into *E. coli*. and express protein by methods known in the art (see, for example, Sambrook and Russell, supra). One may perform this step for all genes identified, or a subset based on results of homology searches, or other criteria.

The proteins can then be tested either before or after purification for functions of commercial interest. Such functions could include but are not limited to (1) insecticidal activity (2) ability to degrade enzyme substrates such as cellulose, hemicellulose, lignin, keratin, starch, etc. (3) ability to stimulate cell proliferation (4) ability to stimulate or suppress immune response, or stimulate or repress activity of proteins involved in immune response (5) ability to confer immunity against challenge by foreign protein or cell (6) ability to induce or prevent cell death such as that created by apoptotic responses (7) ability to inhibit microbial and fungal growth, in particular discovery of novel antibiotic genes.

Notwithstanding the uses described herein, this method will result in the identification of novel genes, and these novel genes will be identified and found to be of use. Enzymes are one type of useful product likely to be found in this method. Accordingly, genes that encode enzymes will be identified. Such genes include enzymes belonging to the family of oxidoreductases, transferases, hydrolases, lyases, isomerases or ligases, as well as lignocellulose-degrading enzymes. Additionally other proteins such as insecticidal proteins, cry proteins, virulence factors, avirulence factors, binding proteins, structural proteins, and receptor proteins will also be discovered by this method.

The method of the invention is a more rapid and efficient method than currently available. Current methods for discovering genes fall into two classes: functional methods and genomic methods. Functional methods attempt to identify genes by virtue of the activity of the gene product, either as naturally expressed from an organism, or after cloning and expression in a heterologous host, such as *E. coli* or yeast. Examples of functional methods include cloning of cDNAs into expression vectors followed by assay for function, and identification of interacting proteins by a two-hybrid screen.

Genomic methods strive to identify novel genes by either (a) identifying genes with significant DNA similarity to known genes of interest; e.g. by hybridization, or by oligo capture techniques, (b) by expression at time or in a tissue of interest; for example in amyloid plaques generated in Alzheimer's patients, or (c) by identifying the sequence of interesting genes after bulk sequencing of the genome. Examples of current methods are described by Lan and Reeves (2000) *Trends in Microbiology* 8:396-401. This review describes many ways in which one may compare two related species to identify differences. Included are description of using differential hybridization, use of microarrays, and polymorphism mapping. The use of microarrays allows comparison of several species (the test strains) to a known, sequenced species (the reference strain). In order to perform this method, one must generate the entire DNA sequence of a genome (the reference genome), then synthesize oligonucleotides corresponding to much of the reference genome, and imbed these oligonucleotides onto a matrix, such as a chip. This process is less desirable for rapid determination of plasmid-encoded genes of commercial value than the proposed method for several reasons. One drawback is that one must have the DNA sequence of a closely related reference strain, and one must synthesize chips containing many oligonucleotides. Further, one can only identify regions of similarity; regions of non-similarity must be inferred. Furthermore, this method does not provide a method to determine the DNA sequence of the variant regions present in the test strain.

Polymorphism mapping for example by digestion with rare restriction enzymes and separation of the resulting fragments on pulsed field (PFGE) or field inversion gels (FIGE) can be used to screen related strains to determine the relative level of relatedness, and to map regions that are dissimilar between strains. However, this method does not generate any sequence information about the novel regions present in strains, and does not identify genes of commercial value. Differential hybridization techniques have the ability to identify regions of difference between strains, and to identify clones likely to contain differences. However, differential hybridization techniques are well known for their technical difficulty. Furthermore, the presence of repetitive DNA elements in genomes can substantially interfere with this method. Differential hybridization techniques based on hybridization of bulk PCR reactions are somewhat more technically feasible. However, none of these techniques has been used for rapid testing of plasmid sequences.

Sequences of several bacterial plasmids have been obtained, increasingly in the course of genome sequencing projects. A listing of bacterial plasmids sequenced to date is currently maintained by the National Center for Biotechnology Information (NCBI) and can be referenced at the NCBI website found on the world wide web at ncbi.mln.nih.gov/PMGifs/Genomes/eub_p.html.

One can readily see that large bacterial plasmids are relatively common in bacteria, and are likely to be present in a great many strains.

TABLE 1

Sequencing plasmid genomes vs. microbial genomes

| Genome | Size of genome | Fold coverage needed | Bp to sequence | Relative Efficiency of new method |
|---|---|---|---|---|
| Large/complex plasmid genome | $1 \times 10^6$ | 8 | $8 \times 10^6$ | 5-fold |
| Small/less complex plasmid genome | $2 \times 10^5$ | 8 | $1.6 \times 10^6$ | 25-fold |
| Bacteria genome | $5 \times 10^6$ | 8 | $4 \times 10^7$ | — |

TABLE 2

Calculation of clones needed to cover plasmid genomes

| Average Clone size (bp) | Approx. size of plasmid genome (bp); assuming 10 plasmids of 100 kb size | Fraction of Genome per clone | Number of clones needed to represent plasmid genome 95% confidence)* | Number of sequencing reactions to sample genome |
|---|---|---|---|---|
| 20,000 | $1 \times 10^6$ | $2 \times 10^{-2}$ | 148 | 296 |
| 15,000 | $1 \times 10^6$ | $1.5 \times 10^{-2}$ | 198 | 396 |
| 10,000 | $1 \times 10^6$ | $1.0 \times 10^{-2}$ | 298 | 596 |
| 5,000 | $1 \times 10^6$ | $5.0 \times 10^{-3}$ | 597 | 1194 |
| 1,000 | $1 \times 10^6$ | $1.0 \times 10^{-3}$ | 2994 | 5988 |
| 800 | $1 \times 10^6$ | $8.0 \times 10^{-4}$ | 3745 | 7490 |

*$N = \ln(1-P)/\ln(1-f)$
P = desired probability
F = fraction of genome in any given clone
N = necessary number of clones in library The following examples are offered by way of illustration and not by way of limitation.

EXPERIMENTAL

Example 1

Rapid Capture of Diversity From *Bacillus Thuringiensis* Strains

The following is an example of how one might practice the invention in the case of a strains or strains where there is likely to be little redundancy with previously known sequences:

Purification of Episomal DNA From a *Bacillus* Culture

To clone and sequence plasmid DNA from a *Bacillus* strain one first needs to prepare purified plasmid DNA. Ideally, one will purify 100 ug or more of purified plasmid DNA. A starter culture of the *Bacillus* strain should be grown in 5 ml of LB overnight at 37° C. with aeration. This 5m1 culture is then used to inoculate a 100-250 ml culture which should be grown for 8 hours at 37° C. with aeration. The young cells in this culture will be easier to lyse. The cells can be harvested at 6000 rpm in a Sorval SS34 rotor for 15 minutes. The cell pellet should be resuspended in 20 ml STE (10 mM Tris pH8, 0.1M NaCl, 1 mM EDTA pH8) to remove all media and then centrifuged again at 6000 rpm for 15 minutes. After removing all traces of the STE, the cell pellets may be frozen overnight. The thawed pellets should be resuspended by vortexing in an appropriate amount of 50 mM Tris pH8.0, 10 mM EDTA pH8, 50 mM glucose and 100 ug/ml RNaseA. Use 5 ml of this buffer for every 100 ml of cell culture. A large amount of powdered lysozyme should be added to the resuspended cells. Incubating the cells at 37° C. for at least one hour helps improve cell lysis. After incubation with lysozyme the cells are lysed by alkaline lysis. 15 ml of 200 mM sodium hydroxide and 1% SDS should be added per 100 ml of cell culture to

TABLE 3

Estimates of advantage of novel system over current methods

| Average Clone size (bp) | Number of clones needed to represent plasmid genome (95% confidence) | Number of sequencing reactions to sample genome | Percent of clones detected as novel | Clone to sequence | Number of sequencing reactions to finish sequence of each novel clone (est. 1.5/kb) | Estimated seq reactions per genome | Efficiency vs sequence of random 800 bp inserts (7490 reads; see table 2) shown as % of reactions | Fold improvement |
|---|---|---|---|---|---|---|---|---|
| 20,000 | 148 | 296 | 50 | 74 | 30*74 = 2220 | 2220 + 296 = 2516 | 33% | 3-fold |
| | | | 10 | 15 | 30*15 = 450 | 450 + 296 = 746 | 10% | 10-fold |
| | | | 1 | 2 | 30*2 = 60 | 60 + 296 = 356 | 4.7% | 20-fold |
| 15,000 | 198 | 396 | 50 | 99 | 22.5*99 = 2228 | 2228 + 396 = 2624 | 35% | 3-fold |
| | | | 10 | 20 | 22.5*20 = 450 | 450 + 396 = 846 | 11% | 8-fold |
| | | | 1 | 2 | 22.5*2 = 45 | 45 + 396 = 441 | 5.9% | 16-fold |
| 10,000 | 298 | 596 | 50 | 149 | 15*149 = 2235 | 2235 + 596 = 2831 | 38% | 2.5-fold |
| | | | 10 | 30 | 15*30 = 450 | 450 + 596 = 1046 | 14% | 7-fold |
| | | | 1 | 3 | 15*3 = 45 | 45 + 596 = 641 | 8.5% | 12-fold |
| 5,000 | 597 | 1194 | 50 | 597 | 7.5*597 = 4477 | 4477 + 1194 = 5671 | 76% | 1.3-fold |
| | | | 10 | 119 | 7.5*119 = 893 | 893 + 1194 = 2087 | 28% | 3.6-fold |
| | | | 1 | 12 | 7.5*12 = 90 | 90 + 1194 = 1284 | 17% | 5.8-fold |
| 1,000 | 2994 | 5988 | 50 | 2994 | 1.5*2994 = 4491 | 4491 + 5988 = 10479 | 139% | 0 |
| | | | 10 | 599 | 1.5*599 = 899 | 899 + 5988 = 6887 | 92% | 0 |
| | | | 1 | 60 | 1.5*60 = 90 | 90 + 5988 = 6078 | 81% | 1.2-fold |

+based on 20 kb insert; 4 kb vector, with average distance of 800 bp between Tn insertions ensure complete lysis. Mix by inversion and incubate at room temperature for 5 minutes. 15 ml of 3M potassium acetate pH 5.5 should be added per 100 ml of cell culture and mixed by inversion. The precipitate should be removed by centrifugation at 13,000 rpm for 30 minutes in the Sorvall SS34. The supernatant should be filtered through a piece of Whatman paper pre-wetted with dH$_2$0. A Qiatip-500 column should be equilibrated with 10 ml Buffer QBT. The filtered supernatant should be applied to the column and the flow-through discarded. The column should be washed twice with 30 ml Buffer QC. The DNA should be eluted from the column with 15 ml of Buffer QF that has been warmed to 65° C. 10.5 ml of isopropanol should be added to the eluted DNA. The DNA is precipitated overnight at –20° C., and the precipitated DNA is centrifuged at 13000 rpm in the Sorvall SS34 rotor for 45 minutes. The supernatant removed and the pellet is washed in 10 ml 70% ethanol. Centrifuge 30 minutes at 13000 rpm. The pellets are dried at room temperature then resuspended in 1 ml of TE (10 mM Tris, 1 mM EDTA, pH 8.0). Resuspend the pellet overnight at 4° C. to ensure dissolution of the plasmid DNA. Check for the presence of plasmid DNA by electrophoresing 10 ul of the plasmid DNA on a 0.5% agarose gel (pulse-field grade agarose) in 1× TAE at 1.5-2 V/cm.

Phase I Screening of a Clones, and Dataset Buildup

A 100 ug aliquot of plasmid DNA is added to nebulizing buffer 50% glycerol and TM buffer (50 mM Tris, 8.1 mM MgSO4 pH7.5) to a volume of 2 ml. The solution is added to the bottom of a nebulizer and incubated for 10 minutes in an ethanol—dry ice mixture. The nebulizer is connected to a nitrogen tank and pressure is applied to the sample in a range of 8 to 12 psi, varying from sample to sample. The sheared DNA is then divided into 8 portions and ethanol precipitated. The DNA is then resuspended in TE and end repaired using T4 polymerase, Kienow and T4 polynucleotide kinase. The end repaired DNA is then electrophoresed for size separation on a 1% low melt agarose gel at 75V for 2.5 hours. The DNA of desired size is excised from the gel, and extracted from the agarose using QIAQUICK® Gel Extraction kit (Qiagen) and subsequently concentrated by ethanol precipitation. The DNA is checked for quality and quantity on a 1% agarose gel run at 100V for 1 hour.

Fragmented, end-repaired, purified DNA is ligated into a suitable vector. For example, BLUESCRIPT™ (Stratagene) or pZERO-2™ (Invitrogen) can be prepared by digesting with an enzyme generating a blunt end (e.g. EcoRV). The terminal phosphates on the ends of the vector may be removed with calf intestinal phosphatase to reduce background colonies resulting from religation of vector. The ligations are performed at 12 degrees Celsius overnight and heat inactivated at 70° C. for 25 minutes. Alternatively ligations are performed with an overnight incubation at 25° C. Transformations are performed by adding 1 ul of the ligation mix to an aliquot of 30 ul of DH10B cells. The cell/DNA mixture is transferred to a cuvette that has been incubated on ice for 10 minutes. The cuvette is placed in the BioRad electroporator and given a voltage of 1700 for 5 ms. SOC is added at a volume of 1 ml to the cuvettes to recover the cells. The cells are transferred to culture tubes and incubated at 37° C. for 1 hour. The transformations are plated onto LB agar containing the appropriate antibiotic.

The colonies are picked into 96 well growth blocks containing 800 ul of Terrific Broth with antibiotic. The blocks are covered with Qiagen Airpore tape and grown overnight at 37° C. with shaking. Glycerol stocks of the growth are prepared by taking 20 ul of the culture and adding it to 20 ul of 40% glycerol. These are stored at –80° C. The 96 well cultures are centrifuged at 4000 rpm for 10 minutes in a refrigerated tabletop centrifuge.

Clone preparation is carried out in 96 well blocks using an alkaline lysis protocol with a Whatman 96 well filter plate for lysate clearing. The DNA is then precipitated, resuspended in water, and run on a 0.8% agarose gel for quantification. The sequencing reactions are performed by cycle sequencing using Applied Biosystems Big Dye Terminator kits and MJ tetrad thermocyclers. The reaction is precipitated and run on ABI 3700 capillary sequencer for analysis.

Sequences resulting from reactions run through the ABI sequencer are transferred to a Sun workstation running a UNIX® operating system. The sequences are checked for quality score, trimmed to remove vector sequences, and assembled using the Phred/Phrap program suite. The sequences of all resulting contigs as well as all unassembled sequences are combined in a directory that acts as a database.

Phase II. Use of Dataset to Rapidly Screen for Novel Gene Regions and Capture Diversity.

In phase II, libraries of closely related species (for example *Bacillus thuringiensis komamtoensis*) or unknown strains verified to be related to *Bacilus thuringiensis* (e.g. by 16sRNA sequnce analysis or MIDI analysis of cell wall fatty acid composition) are generated as described in STEP 2 of the method. For example, one performs a partial digest of plasmid DNA with the enzyme Eco509I which generates a 5' overhang compatable with the restriction enzyme EcoRI. DNA migrating at a size of 5-25 kb, or more preferably 10-20 kb or more preferably 15 kb are excised, and ligated into a vector. One suitable vector would be pBluescript, digested with ecoRI. Alternatively, one may use a cloning vector such as pBeloBAC11 to accept large inserts. Alternatively, one may develop and utilize specialized vectors to allow generation of plasmid clones with inserts of 10-20 kb. In any case, the insert DNA is ligated to the vector, and the ligation transferred into *E.coli* using methods known in the art (e.g. Sambrook and Russell, supra) or by following manufacturer's instructions.

Regardless for the vector, clones from the resulting library are picked at random and grown in 96 well format, and DNA prepared as described above. Sequencing reactions are performed on one or both side of the clone, and the resulting sequences are tested against the existing database of plasmid sequences (from a Phase I project(s)). Clones having at least one unique end sequence are identified for further processing. This DNA is then digested with one of two restriction enzyme that flank the insert but are likely to occur rarely (for example NotI or PmeI) after inactivating the restriction enzymes the two digests are pooled. These pooled reactions are then mutagenized with Tn5 in vitro . One way in which one can achieve this by using a commercially available kit, for example by using the EZ::TN™ Insertion Kit (Epicentre). After mutagenizing and removing transposase (for example by phenol:chloroform extraction followed by ethanol precipitation) reactions are ligated with T4 DNA ligase and transferred into *E.coli*. Clones which receive a transposon insertion are identified by antibiotic resistance (the transposon encodes either kanamycin or tetracycline resistance). Antibiotic resistant clones are picked, and their end-sequences determined as described previously. One chooses a sufficient number of clones to adequately cover the sequence of the novel clones. The number one chooses depends on the size of the clones, and the number of reads per DNA length one desires. One may choose to determine high quality sequence for each nucleotide of each clone. Alternatively one may not wish to determine the nucleotide sequence of each clone. It may be sufficient to sample the clone sequence such that one has reasonable probability of identifying a commercially valuable gene.

Example 2

Capture of Episomal Diversity From Environmental Samples

In this example, one isolates plasmid DNA from a soil, water, or other type of environmental sample, and then generates and screens libraries by end sequencing to identify novel DNA regions. One may sequence either one or both ends of the resulting clones.

Plasmid DNA from soil for example is isolated by the procedure listed above, and further purified by Cesium chloride centrifugation. Purified plasmid DNA is fragmented, and 10-20 kb fragments as well as other size fragments (1-3 kb, 3-10 kb and 10-25 kb) are isolated by agarose gel electrophoresis. Alternatively, one may use vectors that do not require gel purification of fragments to achieve size selection. Purified fragments are ligated to a vector or vectors of choice, and the resulting mixture transferred into *E. coli*. Individual colonies are picked, and DNA prepared for sequencing as above. Resulting sequence is tested for novelty against a database, and novel sequences are identified as described. Novel sequences are then added to the database.

Example 3

Algorithm for Data Parsing

Algorithms are useful to sort data, and to manage large amounts of information. One possible algorithm that may be used to identify clones for further sequencing is described here. This type of algorithm can be particularly useful in cases where one has generated a large dataset of existing sequences (such as bacterial plasmid sequences), and wishes to sequence only clones that do not have identify or high similarity to members of the database.

Algorithm
1. Assign a label to each clone
2. Send sequences to pool 'A'
3. Pre-blast sequences in pool 'A' to remove/mask sequences that are repetitive in nature. (e.g. transposon sequences or vector sequences.) Send these sequences to pool 'B'
4. Blast search of n number sequences in pool 'B'
5. Place sequences in pools based on results of blast search of pool 'B'
   a. If e>10-1, then send to pool 'Failblast'
   b. If<e10-1, then send to pool 'C'
   c. Of Clones in pool 'C' if score<10-10, send to pool 'D'. If>10-10, then send to pool 'Failblast-10'
   d. Of clones in pool 'D', if score<10-50, send to pool 'E' If>10-50, then send to pool 'Failblast-50'
   e. Of clones in pool 'E', if score<10-100, send to pool 'F' If>10-100, then send to pool 'Failblast-100'
   f. Of clones in pool 'F' if score=0.0, send to pool 'Identical'. If score is not 0.0, send to 'Failblast-not identical'
6. Set clones into pools based on cumulative results of blast of both (or multiple) end sequences.

For each sequence in pool 'Failblast', does the sequence have a partner sequence in pool B? If so, sort based on homology of both.
   a. If sequence in pool Failblast does not have a partner sequence in pool 'B' then send the clone to clonepool 'B-9'
   b. If the sequence does have a partner sequence,
   c. If the partner sequence is in pool 'failblast', then place the clone in clonepool 'B-1'.
   d. If the partner sequence is in pool 'FailBlast-10', then place the clone in clonepool 'B-2'.
   e. If the partner sequence is in pool 'FailBlast-50', then place the clone in clonepool 'B-3'
   f. If the partner sequence is in pool 'FailBlast-100', then place the clone in clonepool 'B-4'
   g. If the partner sequence is in pool 'FailBlast-not identical', then place the clone in clonepool 'B-5'.
   h. If the partner sequence is in pool 'Identical', then place the clone in clonepool 'B-6'.

Repeat Operation 1 for Each Sequence in Pool Failblast-10
   a. If sequence in pool Failblast-10 does not have a partner sequence in pool 'B' then send the clone to clonepool 'C-9'
   b. If the sequence does have a partner sequence,
   c. If the partner sequence is in pool 'failblast', then ignore the clone (since it should already be in clonepool 'B-2'.
   d. If the partner sequence is in pool 'FailBlast-10', then place the clone in clonepool 'C-2'.
   e. If the partner sequence is in pool 'FailBlast-50', then place the clone in clonepool 'C-3'
   f. If the partner sequence is in pool 'FailBlast-100', then place the clone in clonepool 'C-4'
   g. If the partner sequence is in pool 'FailBlast-not identical', then place the clone in clonepool 'C-5'.
   h. If the partner sequence is in pool 'Identical', then place the clone in clonepool 'C-6'.

Repeat Operation 1 for Sequences in Pool Failblast-50
   a. If sequence in pool Failblast-50 does not have a partner sequence in pool 'B' then send the clone to clonepool 'D-9'
   b. If the sequence does have a partner sequence,
   c. If the partner sequence is in pool 'failblast', then then ignore the clone (since it should already be in clonepool 'B-3').
   d. If the partner sequence is in pool 'FailBlast-10', then ignore the clone (since it should already be in clonepool 'C-3').
   e. If the partner sequence is in pool 'FailBlast-50', then place the clone in clonepool 'D-3'
   f. If the partner sequence is in pool 'FailBlast-100', then place the clone in clonepool 'D-4'
   g. If the partner sequence is in pool 'FailBlast-not identical', then place the clone in clonepool 'D-5'.
   h. If the partner sequence is in pool 'Identical', then place the clone in clonepool 'D-6'.

Repeat Operation 1 for sequences in pool Failblast-100
   a. If sequence in pool Failblast-100 does not have a partner sequence in pool 'B' then send the clone to clonepool 'E-9'
   b. If the sequence does have a partner sequence,
   c. If the partner sequence is in pool 'failblast', then ignore the clone (since it should already be in clonepool 'B-4').
   d. If the partner sequence is in pool 'FailBlast-10', then ignore the clone (since it should already be in clonepool 'C-4').
   e. If the partner sequence is in pool 'FailBlast-50', then ignore the clone (since it should already be in clonepool 'D-4')
   f. If the partner sequence is in pool 'FailBlast-100', then place the clone in clonepool 'E-4'
   g. If the partner sequence is in pool 'FailBlast-not identical', then place the clone in clonepool 'E-5'.
   h. If the partner sequence is in pool 'Identical', then place the clone in clonepool 'E-6'.

Repeat Operation 1 for Sequences in Pool Failblast-not Identical
  a. If sequence in pool 'Failblast-not identical' does not have a partner sequence in pool 'B' then send the clone to clonepool 'E-9'
  b. If the sequence does have a partner sequence,
  c. If the partner sequence is in pool 'failblast', then ignore the clone (since it should already be in clonepool 'B-5').
  d. If the partner sequence is in pool 'FailBlast-10', then ignore the clone (since it should already be in clonepool 'C-5').
  e. If the partner sequence is in pool 'FailBlast-50', then ignore the clone (since it should already be in clonepool 'D-5')
  f. If the partner sequence is in pool 'FailBlast-100', then ignore the clone (since it should already be in clonepool 'E-5'
  g. If the partner sequence is in pool 'FailBlast-not identical', then place the clone in clonepool 'F-5'.
  h. If the partner sequence is in pool 'Identical', then place the clone in clonepool 'F-6'.

Repeat Operation 1 for Sequences in Pool Identical
  a. If sequence in pool Identical does not have a partner sequence in pool 'B' then send the clone to clonepool 'G-9'
  b. If the sequence does have a partner sequence,
  c. If the partner sequence is in pool 'failblast', then ignore the clone (since it should already be in clonepool 'B-6').
  d. If the partner sequence is in pool 'FailBlast-10', then ignore the clone (since it should already be in clonepool 'C-6').
  e. If the partner sequence is in pool 'FailBlast-50', then ignore the clone (since it should already be in clonepool 'D-6')
  f. If the partner sequence is in pool 'FailBlast-100', then ignore the clone (since it should already be in clonepool 'E-6')
  g. If the partner sequence is in pool 'FailBlast-not identical', then ignore the clone (since it should already be in clonepool 'F-6').
  h. If the partner sequence is in pool 'Identical', then place the clone in clonepool 'G-6'.

7. Report generation and parsed files.

One can combine Clonepools based on desired set for analysis. For example, to receive only the most unique clones, output could contain Clonepools B-1, B-2, B-3, B-9, C-2, C-3 and D-4. For example, a printout is created of all members starting with pool B-1, and progressing to pool G-6. Parsing can be a simple command such as "copy all files with sequence in clone pools B, C, D to directory 'Novel sequences-date'" wherein the directory is created, and sequences passing test are copied to new directory. Similarly, non-novel sequences can be parsed to a different directory, for example "previously identified." Alternatively, the clone pools passing the criteria may be sent to other programs that further process the information. For example, one may wish to search sequences for those with some homology (but not identity) to known genes of interest. One may accomplish this by for example, testing clonepools in searches that involve hypothetical translation of the DNA sequence; typically in all 6 possible reading frames.

Example 4

Plasmid DNA from strain ATX13026 was prepared by growing and harvesting the cells in a large culture. The plasmid DNA was extracted by treatment of cell pellet with 4%SDS for 30 minutes, neutralization with Tris, and a subsequent incubation with 20 mM NaCl on ice. The DNA was precipitated by isopropanol precipitation and then further purified by CsCl centrifugation. Purified plasmid DNA was sheared by passage through a nebulizer (Invitrogen, Catalog no. K7025-05) using 8 psi for 2.5 minutes. Sheared DNA was separated by size by electrophoresis on an agarose gel, and DNA of the appropriate size excised, and purified by methods known in the art. The 5' and 3' termini of the purified fragments were converted to blunt ends using a treatment with T4 DNA polymerase, Klenow large fragment at 25° C. in the presence of all 4 dNTPs followed by incubation with T4 polynucleotide kinase at 37° C. The blunt end fragments were then ligated into a vector, and transformed into *E. coli*. Individual clones were picked into wells of 96 well plates, and grown to saturation at 37° C. Plasmid DNA was prepared from these cells by methods known in the art, and the DNA sequences of the ends of 10,000 clones were obtained. Sequence files from a number of sequencing reactions were analyzed by phredPhrap/Consed suite of programs. Contigs resulting from this analysis were then tested for presence of novel endotoxins by comparing the sequences against a database of known endotoxin proteins using the BLAST®X algorithm.

TABLE 4

Novel endotoxin-containing clones identified by the method

| Clone | Amino Acid homology to endotoxin |
| --- | --- |
| pAX006 | 33% cry4Aa |
| pAX007 | 36% cry4Aa |
| pAX008 | 67% cry40Aa1 |
| pAX009 | 34% cry8Ba |
| pAX010 | 35% cry36Aa1 |
| pAX014 | 55% cry40Aa1 |

Using this sampling, the clones containing homologies to endotoxins were identified and sequenced in the regions predicted to containing endotoxin genes. Sequence analysis of the open reading frames obtained by this sequencing identified novel endotoxin genes. The genes identified by this method are not likely to hybridize to the set of known genes, due to the low level of amino acid and DNA homology between these genes and known genes.

Example 5

Identification of a Novel Cellulase

A database of cellulases, xylanases and other lignocellulose degrading enzymes was created from existing known amino acid sequences. The database of end sequences from strain ATX13026 was tested for presence of lignocellulose degrading enzymes. Clone pAXE001 was found to have strong homology to a known cellulases.

TABLE 5

Novel Cellulase identified by the method

| Clone | Amino Acid homology to cellulase |
| --- | --- |
| pAXE001 | 84% to cellulase, GENBANK ® accession number A44808 |

Example 6

Construction of miniCos-I

First, Supercos (Stratagene) was linearized with EcoRI, and the 5' overhangs filled by incubation with Klenow and dNTPs as known in the art (Sambrook and Russell, supra). The linearized vector was then digested with Hpa I. The 5.5 kilobase fragment containing the COS sites, kanamycin resistance gene, and the SV40 replication origin was purified by agarose gel electrophoresis.

Oligonucleotides were designed such that a PCR reaction using oligo 1 and 2 amplified a portion of Supercos containing the origin of replication and ampicillin resistance gene. Oligo 1 incorporated single lox site, and a SwaI site oriented such that the PCR product contains a lox site internal to a SwaI site. Oligo 2 incorporated a novel multiple cloning site. Using Oligos 1 and 2, a PCR product was generated from Supercos. The PCR product was gel purified, and subjected to a second PCR reaction with oligonucleotide 1 and oligonucleotide 3. Oligo 3 was designed such that it overlapped Oligo 2, and incorporated a lox recombinase site, as well as a SwaI restriction site into the PCR product, oriented as for Oligo 1. The 3' single stranded nucleotides generated by the polymerase were removed by incubation with Klenow fragment of DNA polymerase and dNTPs, and 5' phosphates added by incubation with T4 DNA polynucleotide kinase and ATP as known in the art.

PRE112 from ATCC 87692 (Edwards et al. (1998) *Gene* 207:149-157) was digested with EcoRI, and the fragment containing the sacb gene isolated by agarose gel electrophoresis, and the 5' overhangs filled by incubation with Klenow and dNTPs as known in the art (Sambrook and Russell, supra).

The blunt ended PCR product was ligated to the 5.5 kb fragment of Supercos, transformed into *E. coli*, and DNA of the correct constructs (referred to herein as Tempclone#1) was verified by restriction digestion and DNA sequencing. Tempclone#1 was then digested with SmaI, treated with calf intestinal phosphatase, and ligated to the sacB fragment from PRE112. Clones containing the correct ligation products were identified as known in the art. The presence of the kanamycin resistance, ampicillin resistance, and sacB markers was confirmed by testing in *E. coli*, and a positive clone, referred to herein as Tempclone#2, was identified.

Tempclone#2 was digested with AccIII, and ligated to a DNA linker designed to incorporate restriction sites for the enzymes ApaI and BsiWI into tempclone #2. This yielded Tempclone#3.

By analyzing the DNA sequence of lambda phage, a DNA region approximately 9 kb in size was identified that lacked restriction sites for XbaI, SwaI, NotI, and all other enzymes in the multiple cloning site. Lambda DNA (New England Biolabs) was digested with ApaI and BsiWI, and the 9 kb fragment was isolated.

Tempclone#3 was digested with ApaI and BsiWI, ligated to the 9 kb lambda fragment, and transformed into *E. coli*. Clones containing the lambda insert were confirmed by restriction digest. The final clone is referred to as miniCos-I.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for screening a plurality of bacterial plasmid DNA sequences comprising:
   a) generating a library comprising a plurality of bacterial plasmid DNA sequences, wherein said bacterial plasmid DNA sequences are cloned from isolated plasmid DNA;
   b) selecting one or more plasmid DNA sequences from said library;
   c) obtaining a partial sequence for at least a first bacterial plasmid DNA sequence, wherein the length of said partial sequence is less than one-third of the length of the plasmid DNA sequence;
   d) determining if the plasmid DNA sequence is a novel sequence by using an algorithm which:
      i) compares the partial sequence(s) generated in step (c) to a database comprising a plurality of nucleotide sequences; and,
      ii) characterizes each DNA sequence as a novel sequence if the partial sequence for that DNA sequence shares less than 99% sequence identity with each sequence in the database;
   e) obtaining the full sequence of any DNA sequence(s) characterized as novel in step (d);
   f) adding the nucleotide sequence(s) obtained in step (e) to said database in step (b) to generate an updated database; and,
   g) sequentially repeating steps (b)-(f) for one or more additional plasmid DNA sequences.

2. The method of claim 1, wherein said partial sequence obtained in step (c) is translated to obtain all possible amino acid sequences and wherein said amino acid sequences are compared to a database of amino acid sequences.

3. The method of claim 1, wherein the determination in step (d) is based on the partial sequence having less than 30% sequence identity with any sequence in said database of nucleotide sequences.

4. The method of claim 1, wherein the determination in step (d) is based on the partial sequence having less than 60% sequence identity with any sequence in said database of nucleotide sequences.

5. The method of claim 1, wherein the determination in step (d) is based on the partial sequence having less than 80% sequence identity with any sequence in said database of nucleotide sequences.

6. The method of claim 1, wherein the determination in step (d) is based on the partial sequence having less than 90% sequence identity with any sequence in said database of nucleotide sequences.

7. The method of claim 1, wherein said plasmid DNA sequences are about 10 to about 20 kb in size.

8. The method of claim 7, wherein said plasmid DNA sequences are about 15 kb in size.

9. The method of claim 1, wherein said plasmid DNA sequences are about 1 to about 5 kb in size.

10. The method of claim 9 wherein said plasmid DNA sequences are about 1.5 kb in size.

11. The method of claim 1, wherein said plasmid DNA sequences are obtained from bacteria.

12. The method of claim 1, wherein said plasmid DNA sequences are obtained from an organism selected from the group consisting of *Clostridia*, *Bacillus*, *Agrobacterium*, and *Rhizobium*.

13. The method of claim 12, wherein said organism is *Bacillus*.

14. The method of claim 13, wherein said organism is *Bacillus thuringiensis*.

15. The method of claim 1, wherein said nucleotide sequence obtained in step (e) encodes an insecticidal protein.

16. The method of claim 15, wherein said insecticidal protein is a delta-endotoxin.

17. The method according to claim 1, wherein said novel nucleotide sequence encodes a lignocellulose-degrading enzyme.

18. The method of claim 17, wherein said lignocellulose-degrading enzyme is a cellulase.

19. The method of claim 1, wherein said plasmid DNA sequences are assembled into a library, and wherein said library is generated using a vector comprising a stuffer fragment and at least one cos site.

20. The method of claim 1, wherein said database of nucleotide sequences is a publically available database.

21. The method according to claim 1, wherein said database comprises only known endotoxin proteins.

22. The method of claim 1, wherein said database comprises only known lignocellulose-degrading enzymes.

* * * * *